United States Patent [19]

Stricker

[11] Patent Number: 4,943,275
[45] Date of Patent: Jul. 24, 1990

[54] INSERTABLE BALLOON WITH CURVED SUPPORT

[75] Inventor: Saul Stricker, Richmond Hill, Canada

[73] Assignee: Abiomed Limited Partnership, Danvers, Mass.

[21] Appl. No.: 257,752

[22] Filed: Oct. 14, 1988

[51] Int. Cl.⁵ ............................................. A61M 29/00
[52] U.S. Cl. ........................................ 600/18; 604/96; 606/194
[58] Field of Search .................................. 604/96–103, 604/344, 281; 600/18; 128/344; 606/192, 194

[56] References Cited

U.S. PATENT DOCUMENTS 4,033,331  7/1977  Guss et al. .......................... 128/657
4,741,328  5/1988  Gabbay ................................. 600/18

Primary Examiner—Stephen C. Pellegrino
Attorney, Agent, or Firm—Lahive & Cockfield

[57] ABSTRACT

A balloon assembly has an intrinsic curvature adapted to a passage in a blood vessel, and is straightened by a removable stiff member extending within the catheter to facilitate insertion along the passage. When the balloon is at a curved portion of the passage, the stiff member is retracted, allowing the balloon and adjacent support to conform to the curved passage and advance further without trauma to the vessel. The curved balloon may be stably positioned in a curved arterial passage and pumped with a pulsatile inflation source.

18 Claims, 2 Drawing Sheets

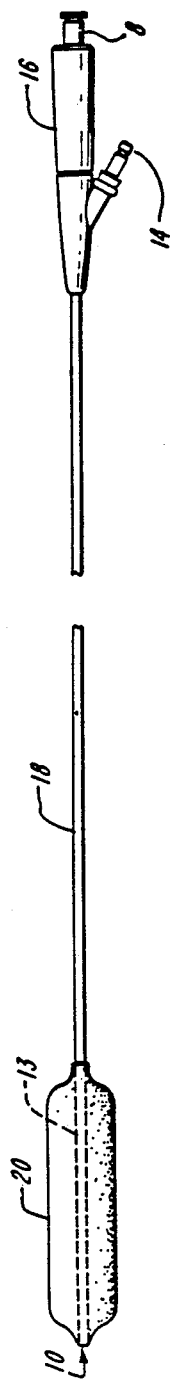
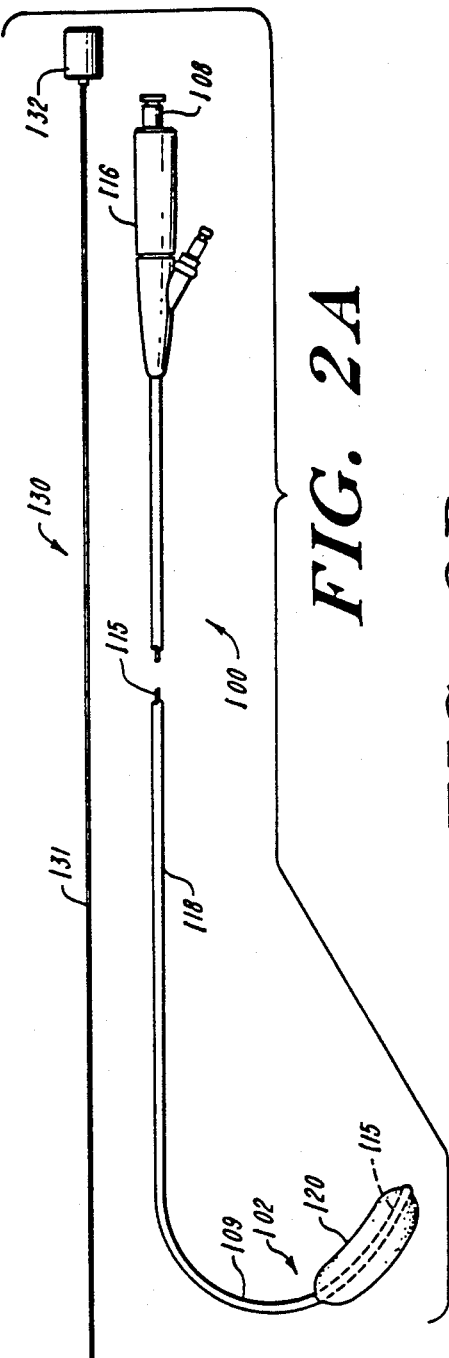
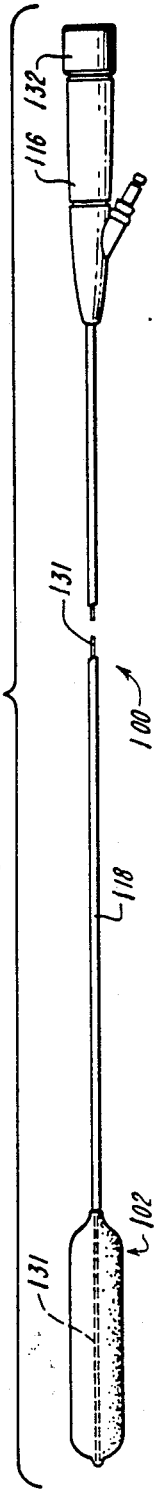
FIG. 1
FIG. 2A
FIG. 2B

INSERTABLE BALLOON WITH CURVED SUPPORT

BACKGROUND OF THE INVENTION

The present invention relates to devices such as intra aortic balloon pumps (IABPs) wherein an inflatable envelope or balloon mounted on the end of a long catheter is inserted through a blood vessel to a position in the aorta where it is operated to supplement the cardiac pumping action.

In a typical prior art construction, a manifold or handle is mounted to provide a separate fluid connection to each of an inner and an outer tube, which extend for a length of one to one and a half meters from the handle. At the far ends of the tubes a balloon is mounted to be inflated by the outer tube, while the inner tube extends through the balloon to provide a lumen for sampling fluids on the far (cardiac) side of the balloon. Commonly, the balloon is about the size and shape of a long hot dog, although other balloon designs are known.

Insertion of the balloon to a site in the aorta is accomplished by first compacting the uninflated balloon, by folding, wrapping, twisting or the like, and then inserting the compacted balloon assembly through an artery using a guide wire and/or sheath to guide it past irregularities or branches in the artery. Care must be taken during insertion to avoid trauma or perforation, particularly when the balloon is passing branches or curves of the artery.

Because the inflatable balloon is fabricated of a preshaped thin membrane of low intrinsic stiffness, it is customary to provide a support member within the balloon to hold the balloon extended in the longitudinal sense during pumping. This support member, which may simply be the end portion of the inner tube, or which may include a separate wire or wire-wrapped reinforcement, limits the ability of the balloon and to follow or conform to a curved arterial passage, and does not permit the balloon to remain stably positioned in a curved arterial section during pumping.

SUMMARY AND OBJECTS OF THE INVENTION

It is an object of the invention to provide an insertable arterial balloon assembly better adapted to be positioned in a curved arterial passage.

It is another object of the invention to provide an insertable arterial balloon assembly having a curved balloon support structure which may be selectively straightened or stiffened, or relaxed and curved, during insertion.

It is another object of the invention to provide a balloon structure which is stably positioned in a curved arterial passage during pumping.

These and other desirable features are achieved in an arterial balloon assembly having an intrinsically curved structure at the balloon end. A straightening member is inserted through the inflation manifold to the balloon for causing the assembly to straighten out. In this configuration the assembly is adapted for insertion through an artery; when the straightening member is drawn back a few centimeters the balloon end re-assumes its predetermined intrinsic flexibility and curvature. In the relaxed or curved configuration, the balloon may lie quiescent in, or be advanced to a curved arterial path. In a preferred embodiment, the curvature conforms to the sharply curved passage between the ascending and descending aorta. During pumping, the curvature eliminates creeping of the balloon characteristic of a straight balloon structure.

BRIEF DESCRIPTION OF THE DRAWINGS

FIG. 1 shows a prior art intra aortic balloon pump;

FIGS. 2A-2C show corresponding views of an intra aortic balloon pump according to the present invention.

DETAILED DESCRIPTION

Figure 2C:
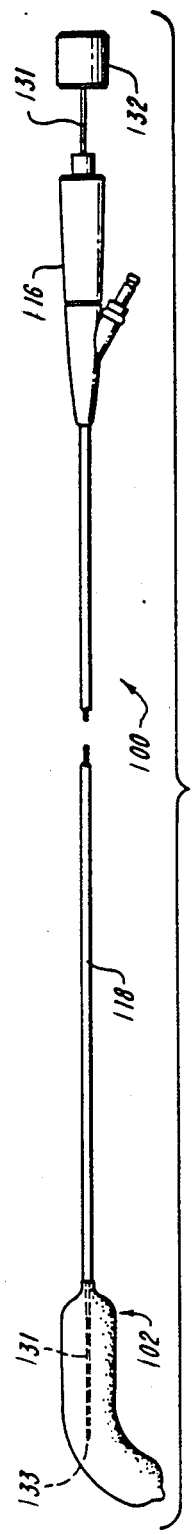

By way of background, FIG. 1 shows a prior art IABP which has a balloon 20 mounted on an inflation catheter 18 extending from a handle 16 which serves as a fluids manifold for connection to a pulsed source of inflation fluid, via port 14. Catheter 18 may carry an interior tube (not shown) which interconnects a fluid sampling port 10 at the distal end of the balloon with a second port 8 in the handle 16. In the prior art IABP the catheter 18 and an interior tube or balloon supporting member 13 each assume a straight profile in their relaxed state, although they are of sufficient flexibility to allow lateral bending for insertion as they follow a sheath or guide wire. It is also known in the art to provide a relatively stiff torquing wire or rod which extends from the handle to the balloon tip for twisting the balloon to compact it.

By contrast, the presently preferred embodiment of the invention disclosed herein, illustrated in FIG. 2A, is an IABP assembly 100 wherein the balloon end 102 is formed with an intrinsic curvature in the region of the balloon 20 and preferably extending to the adjacent portion 109 of the inflation catheter 118. In FIG. 2A, a tube 115 forming the inner lumen of the preferred embodiment is shown in phantom; the portion of tube 115 within the balloon serves to support the distal balloon end in longitudinal extension and prevent collapse, and thus constitutes a support structure. In other embodiments the balloon support structure may consist of a spiral wound wire tube or the like. According to the present invention, the balloon end is provided with a non-straight, and preferably curved balloon-supporting structure. A separate stiff straightening member 130, shown removed from the assembly, is adapted to fit within the catheter 118 for straightening the end during the initial stages of balloon insertion. The member 130 fits in through a central port, e.g., the fluid sampling port 108 in the illustrated two-lumen assembly, and its elongate solid or tubular stiffening rod 131 extends to the balloon tip.

FIG. 2B shows the assembly of FIG. 2A with the straightening member 130 fully inserted. For clarity of illustration, tube 115 is not shown, although it will be understood that in the embodiment under discussion stiffener 131 extends within, and is constrained by, that tube. The stiffness of stiffener 131 overcomes the intrinsic curvature of the different supporting members at the balloon end 102 of the device, and thus straightens the end. Knob 132 at the near end of member 130 locks to a mating fitting on the handle 116 by a bayonette mount, locking Luer fitting, or the like, to secure the member in position.

FIG. 2C shows the assembly of FIG. 2B with the straightening member 130 withdrawn a slight amount, about two to five centimeters, to allow the balloon end to partially re-assume its normal curvature. As shown, the end 133 of the straightening rod 131 is retracted from the balloon tip, and resides within the balloon. In this position, the balloon may be advanced around a sharply curved arterial path. When the rod 131 is withdrawn further, the balloon assembly reassumes its fully curved shape illustrated in FIG. 2A, and may be advanced along a curved path of greater length.

In a preferred embodiment of the invention, a balloon is inserted into the ascending aorta by first straightening the assembly as shown in FIG. 2B and advancing the catheter along an arterial path into the descending aorta, and then, when the balloon has advanced to the region of the aortic arch, simultaneously withdrawing the straightening member and advancing the curved balloon tip around the arch into the ascending aorta. Preferably the straightening member is withdrawn as the balloon is advanced, so that the tip portion of the assembly advances and curves around the arch simultaneously. This minimizes trauma to the aorta.

Figure 3:
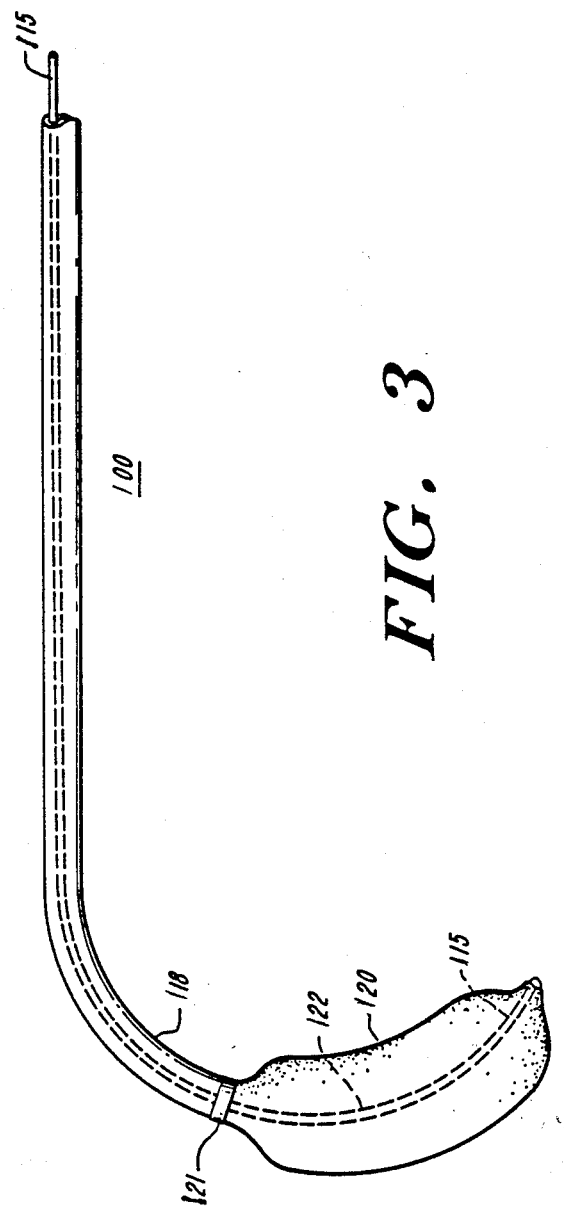
FIG. 3 shows a partial cutaway view of the balloon end of the embodiment of FIGS. 2A-2C.

FIG. 3 illustrates in greater detail the structure of a presently preferred embodiment of the balloon end of the assembly 100. As shown, a strong, curved envelope or balloon 120 is supported at one end by an inflation catheter 118 and at the other end by a fluid sampling tube 115 which extends within catheter 118. Balloon 120 is formed of a strong thin film, and tubes 118, 115 are formed by extrusion from a polyurethane material. In a prototype embodiment, the catheter tube and the support member tubes were formed by extrusion into bulk tubing from the polyurethane materials sold under the trade names "Pellethane" and "Isoplast", respectively, of Dow Chemical Company.

Each of the tubes 118, 115 was first heat-formed to produce at its end portion a radius of curvature of two to five centimeters in a region of the tubing extending over a distance of ten to twenty centimeters from the balloon distal end, and the two tubes were then aligned in a jig with their curvatures parallel. With the tubes held in this alignment, the balloon and handle were then mounted at opposed ends of the assembly. Suitable assembly techniques for attaching the balloon include solvent bonding, RF welding, heat welding, and adhesive or other bonding. During assembly, radio opaque markers are placed at the end of the catheter and on the support member, in a manner known in the art. This permits fluoroscopic visualization of the balloon and its direction of curvature during insertion. Preferably the envelope of balloon 120 was also formed having an intrinsic curvature between its ends matching that of the tubing. While not strictly cylindrical, the balloon ends were centered at the tubes, and in an unstressed state the balloon walls extended in a roughly curved or polygonal arch between the ends. Thus, "curvature", as applied to the balloon herein means simply following a generally curved path along the curved tubes in an unstressed state. The balloon shape was achieved by forming the envelope on appropriate mandrels.

A straightening member was then made up of nineteen gauge regular wall stainless steel tube stock. This stock was found to provide adequate stiffness and resistance to lateral bending to overcome the curvature of the catheter and support tubing. While a solid metal rod, preferably a wire under one millimeter diameter, could also be used, the tubing was preferred because it could be placed over a guide wire to facilitate insertion of the balloon assembly in a blood vessel.

The IABP assembly fabricated in this manner had an intrinsically curved end portion which would re-assume its curved shape when the straightening member was withdrawn. Not only was the IABP more readily insertable around the aortic arch, but the assembly required no steering wires and, since the straightener provided a high degree of stiffness, could employ soft tubing without impairing its ease of insertability.

This completes a description of a preferred embodiment of the invention, and of its mode of insertion, both of which have been described with reference to a double lumen IABP assembly having a balloon dimensioned for insertion in the ascending aorta. It will be understood, however, that the invention comprehends other forms of insertable balloon apparatus, with differing balloons, intrinsic curvatures, number of lumens and having curved or uncurved lengths of adjacent catheter. For example, even a single-lumen device may be so formed.

The invention being thus disclosed, variations and modifications thereof will occur to those skilled in the art, and all such variations and modifications are considered to lie within the scope of the invention, as defined in the claims appended hereto.

What is claimed is:

1. An insertable balloon assembly comprising
a balloon having first and second ends,
a balloon supporting structure extending between the first and second ends of the balloon which maintains the balloon longitudinally extended to prevent collapse of the balloon, and imparting a curvature to said balloon conforming to a curved arterial passage such that the balloon remains stably positioned when pumping in the curved passage,
an inflation catheter having a first end with a curvature matching said supporting structure connected to said balloon second end and extending to a handle assembly which is thereby interconnected with the balloon, said supporting structure defining an inner lumen extending in said catheter for receiving a straightening member inserted through said handle which straightens the balloon for insertion.

2. An assembly according to claim 1, further comprising a straightening member adapted for insertion through said catheter to straighten said supporting structure for insertion of the balloon along a path in a blood vessel.

3. An assembly according to claim 2, wherein said balloon supporting structure has a curved portion with a characteristic radius of curvature in the range of approximately two to five centimeters.

4. An assembly according to claim 2, wherein a curved portion of said supporting structure extends for at least the full length of the balloon.

5. An assembly according to claim 4, wherein said curved portion extends for approximately twice the length of the balloon.

6. An assembly according to claim 4, wherein said curved portion approximately conforms to the curvature of the aortic arch.

7. An assembly according to claim 1, wherein said balloon assembly is a double lumen intra aortic balloon pump assembly.

8. An assembly according to claim 7, wherein said supporting structure conforms to the curvature of the aortic arch.

9. An assembly according to claim 7, wherein said supporting structure includes at least a portion of a fluids sampling tube defining an inner lumen of the double lumen balloon pump assembly.

10. An assembly according to claim 9, wherein the supporting structure further includes at least a portion of the inflation catheter.

11. An assembly according to claim 7, further comprising a straightening member adapted for removable insertion through said catheter to straighten said supporting structure for enabling insertion of the balloon along a path in a blood vessel.

12. An assembly according to claim 11, wherein said supporting structure conforms to the curvature of the aortic arch, such that by withdrawing the straightening member the balloon assumes a curved shape to advance along the aortic arch.

13. A method of inserting a balloon along a passage in a blood vessel, such method comprising the steps of
   (i) providing a curved balloon support which imparts a curvature to the balloon,
   (ii) providing a straightening member, insertable within said balloon,
   (iii) inserting the straightening member to straighten the curved balloon support and thereby straighten the balloon for advancing the balloon a first distance along the passage, and
   (iv) at least partially withdrawing the straightening member to permit curving of the support so that the balloon assumes a curvature and advancing the balloon a further distance to position the balloon in a pumping locus located in a curved portion of the passage, and wherein said curved support conforms to said curved passage so that the balloon remains stably positioned during pumping.

14. A method according to claim 11, wherein step (iv) includes the step of partially withdrawing the straightening member while simultaneously advancing the balloon along the passage.

15. A method according to claim 11, wherein the steps of advancing the balloon advances the balloon to a site past the aortic arch.

16. An insertable balloon assembly comprising
   a balloon having first and second ends,
   a curved balloon support coupled to the first end of the balloon and extending through the balloon to the second end, said balloon support maintaining said balloon longitudinally extended to prevent collapse of the balloon and imparting a curvature to said balloon adapting the balloon to a curved arterial passage, said support having a central lumen,
   an inflation catheter coupled to the second end of the balloon and having a curvature substantially matching the balloon support at said second end,
   a handle assembly connected to said catheter, and
   straightening means insertable through said handle and catheter in the lumen of the support to the balloon for straightening said balloon support so that the balloon may be inserted along an arterial passage.

17. An insertable balloon assembly according to claim 16, wherein the balloon support imparts a curvature to the balloon such that the balloon remains stably positioned in the curved arterial passage during pumping.

18. An insertable balloon assembly according to claim 17, wherein said support has a curvature conforming to the aortic arch.

* * * * *